United States Patent
Neltner

(10) Patent No.: US 12,083,286 B2
(45) Date of Patent: Sep. 10, 2024

(54) SYSTEM AND METHOD FOR GENERATING GANZFELD EFFECT

(71) Applicant: Brian Neltner, Somerville, MA (US)

(72) Inventor: Brian Neltner, Somerville, MA (US)

( * ) Notice: Subject to any disclaimer, the term of this patent is extended or adjusted under 35 U.S.C. 154(b) by 171 days.

(21) Appl. No.: 17/205,082

(22) Filed: Mar. 18, 2021

(65) Prior Publication Data

US 2021/0299397 A1    Sep. 30, 2021

Related U.S. Application Data

(60) Provisional application No. 63/000,156, filed on Mar. 26, 2020.

(51) Int. Cl.
*A61M 21/00* (2006.01)
*A61N 5/06* (2006.01)

(52) U.S. Cl.
CPC ........... *A61M 21/00* (2013.01); *A61N 5/0618* (2013.01); *A61M 2021/0044* (2013.01); *A61N 2005/0648* (2013.01); *A61N 2005/0662* (2013.01)

(58) Field of Classification Search
CPC .......... A61M 21/00; A61M 2021/0044; A61M 2205/3375; A61M 2205/50; A61M 2205/587; A61N 5/0618; A61N 2005/0648; A61N 2005/0662
See application file for complete search history.

(56) References Cited

U.S. PATENT DOCUMENTS

| | | | | |
|---|---|---|---|---|
| 4,777,937 A | * | 10/1988 | Rush | A61M 21/00 600/27 |
| 5,308,246 A | * | 5/1994 | Balocco | A61B 5/16 351/44 |
| 7,703,967 B2 | * | 4/2010 | Parker | G02B 6/0061 362/606 |
| 2020/0269065 A1 | * | 8/2020 | Broeng | H05B 45/20 |

FOREIGN PATENT DOCUMENTS

| | | | | |
|---|---|---|---|---|
| CN | 112206422 A | * | 1/2021 | ........... A61N 5/0618 |
| EP | 1642609 A1 | * | 4/2006 | ........... A61M 21/00 |

* cited by examiner

*Primary Examiner* — Joseph M Dietrich
*Assistant Examiner* — Michael T. Holtzclaw
(74) *Attorney, Agent, or Firm* — AKC PATENTS, LLC; Aliki K. Collins

(57) ABSTRACT

A system for generating a Ganzfeld effect includes a flat light emitting diode (LED) panel emitting strobing light, and a controller for controlling the LED panel strobing light. The controller controls a strobing rate of the emitted strobing light so that the strobing light triggers a Ganzfeld effect to a user standing in front of the flat LED panel. The strobing light is generated by switching on/off a single color light, or by switching between different colors with an off period between alternating colors or without an off period between alternating colors.

22 Claims, 8 Drawing Sheets

Mode 1: Hue varies over time and is turned on and off at 10Hz to 60Hz.

Mode 2: Two (or more) hues alternating with off period in between.

Mode 3: Alternate between two (or more) hues with no off period.

SYSTEM AND METHOD FOR GENERATING GANZFELD EFFECT

CROSS REFERENCE TO RELATED CO-PENDING APPLICATIONS

This application claims the benefit of U.S. provisional application Ser. No. 63/000,156 filed on Mar. 26, 2020 and entitled SYSTEM AND METHOD FOR GENERATING GANZFELD EFFECT, which is commonly assigned and the contents of which are expressly incorporated herein by reference.

FIELD OF THE INVENTION

The present invention relates to a system and a method for generating a Ganzfeld effect and in particular to a system and a method for generating a Ganzfeld effect via a strobing flat LED panel light.

BACKGROUND OF THE INVENTION

The Ganzfeld effect describes a phenomenon perceived by a person when the person is exposed to an unstructured, uniform stimulation field. The stimulation field may be sound, light, electrical, or magnetic. The Ganzfeld effect associated with a visual light signal is caused by staring at an undifferentiated and uniform field of color flickering at a rate in the 10 Hz to 60 Hz range. The Ganzfeld effect is not fully understood neurologically, but is believed to work via flicker phosphenes which produce geometric patterns such as squares and hexagons at lower strobe frequencies and more complex shapes such as pinwheels and spirals at higher strobe frequencies. The underlying source of the specific patterns is most likely related to basic phosphene patterns converted to cortical coordinates to produce "form constants". The Ganzfeld effect can also generate hallucinations and altered states of consciousness.

A "mind" machine utilizes sound pulses, or flashing light or changing electrical or magnetic fields to generate the Ganzfeld effect. In one example, a light and sound mind machine 80 includes a set of headphones 82, a strobe light goggles 84, and a control unit 86, shown in FIG. 1. Other mind machines involve an array of individual white strobe lights shining on a user with their eyes closed. Mind machines may be used for therapeutic, relaxation or mind altering purposes. Most of the currently available "mind" machines utilize stimulation fields that are in very close proximity to a person's eyes and ears, and typically use strobing white light. There is a need for alternative sources of generating the Ganzfeld effect that do not require to be in very close proximity to a person and which fully utilize color.

SUMMARY OF THE INVENTION

The present invention relates to a system and a method for generating a Ganzfeld effect and in particular to a system and a method for generating a Ganzfeld effect via a strobing flat LED panel light.

In general, in one aspect the invention provides a system for generating a Ganzfeld effect including a flat light emitting diode (LED) panel emitting strobing light, and a controller for controlling the LED panel strobing light. The controller controls a strobing rate of the emitted strobing light so that the strobing light triggers a Ganzfeld effect to a user standing in front of the flat LED panel.

Implementations of this aspect of the invention include the following. The flat LED panel is an edge-lit flat LED panel that receives light from an edge along a plane of the flat LED panel and emits light out of the plane of the flat LED panel. The strobing rate is in the range of 10 Hz to 60 Hz. The flat LED panel comprises a red-green-blue (RGB) panel, or a red-green-blue-white (RGBW) panel or other combinations of two or more color panels. The strobing light is generated by switching on/off a single color light. The strobing light is generated by switching between different colors with an off period between alternating colors or without an off period between alternating colors. The strobing light comprises a strobe rate that varies over time. The system further includes a strobe application that provides computer implemented instruction for shifting the colors and hues of the strobing light and for varying the strobing rate in order to generate the Ganzfeld effect. The system further includes additional LED panels and all LED panels are wirelessly synchronized via a low-latency protocol that allows the LED panels to strobe synchronously. The system further includes an antenna, an audio input port, an on/off switch, a sender, a receiver, hardware interfaces, and controls for the strobe rate change, speed of color change, strobing or visualization mode, and brightness of the LED panel. The system further includes an audio signal input and an audio analysis application. The audio analysis application detects beats in the audio signal and varies a beat detection threshold to target a specified number of beats per second. The detected beats per second are used to time-modulate the color, hue, saturation, brightness or strobe rate of the strobing light.

In general, in another aspect the invention provides a system for generating a Ganzfeld effect including a flat light emitting diode (LED) panel emitting light, an audio signal input and an audio analysis application. The audio analysis application detects beats in the audio signal and varies a beat detection threshold to target a specified number of beats per second and the detected beats per second are used to time-modulate color, hue, saturation, or brightness of the LED panel light so that the time-modulated LED panel light triggers a Ganzfeld effect to a user standing in front of the flat LED panel.

In general, in another aspect the invention provides a method for generating a Ganzfeld effect including providing a flat light emitting diode (LED) panel and emitting strobing light via the LED panel, then providing a controller for controlling the LED panel strobing light, and then controlling a strobing rate of the emitted strobing light so that the strobing light triggers a Ganzfeld effect to a user standing in front of the flat LED panel.

The details of one or more embodiments of the invention are set forth in the accompanying drawings and description below. Other features, objects, and advantages of the invention will be apparent from the following description of the preferred embodiments, the drawings and from the claims.

DETAILED DESCRIPTION OF THE INVENTION

The present invention relates to a system and a method for generating a Ganzfeld effect and in particular to a system and a method for generating a Ganzfeld effect via a strobing flat LED panel light.

Figure 1:
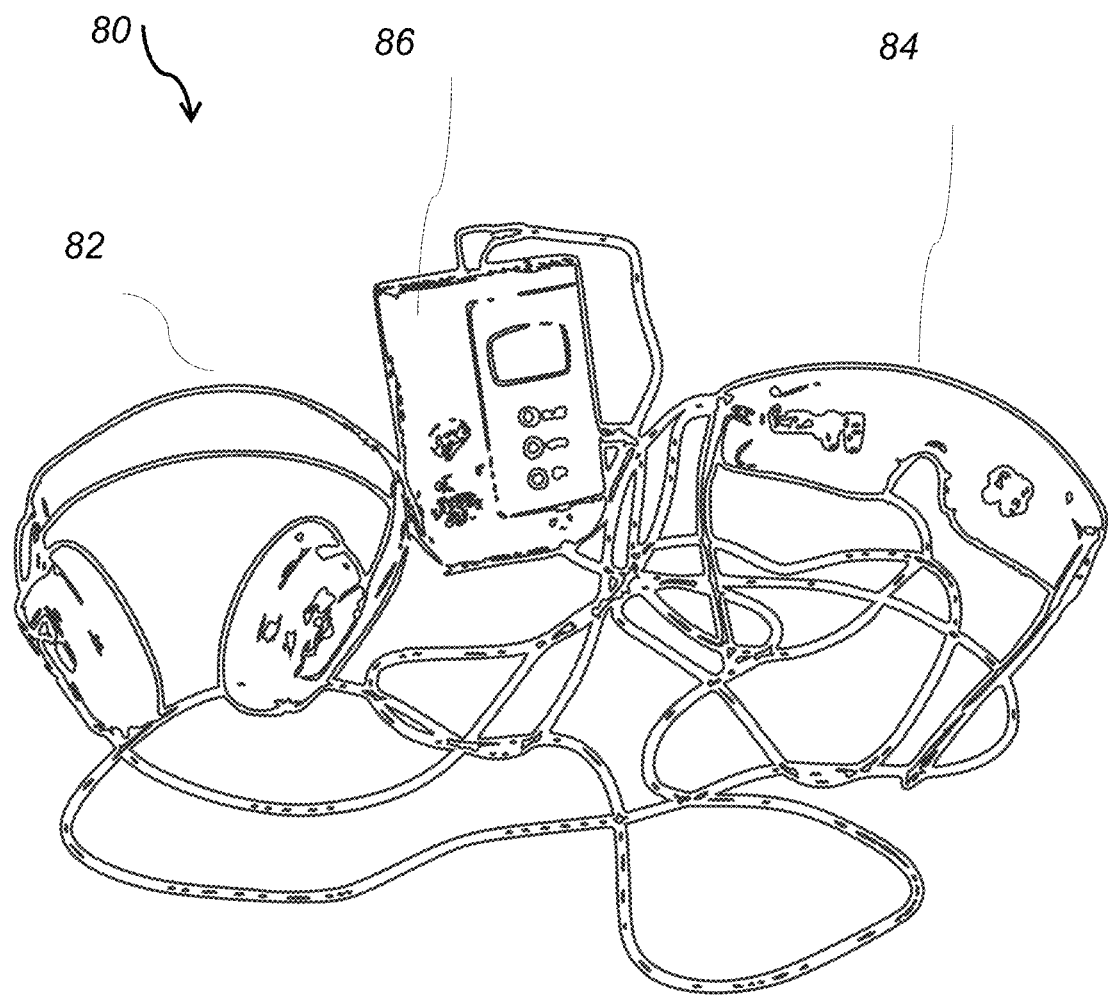
FIG. 1 is prior art Ganzfeld "mind" machine.
Figure 2A:
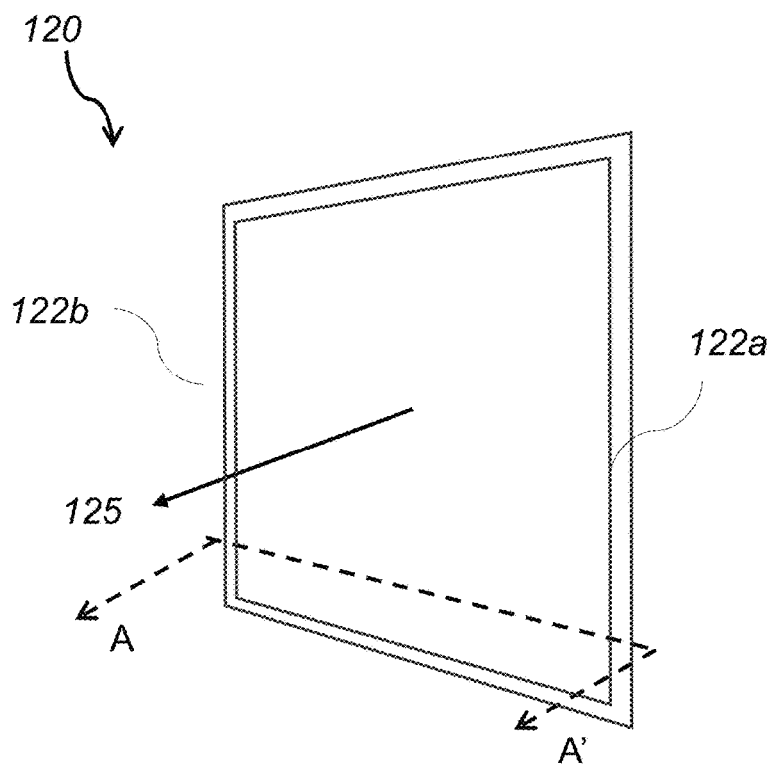
FIG. 2A is a perspective side view of an edge lit flat LED panel light used to generate the Ganzfeld effect according to this invention.
Figure 2B:
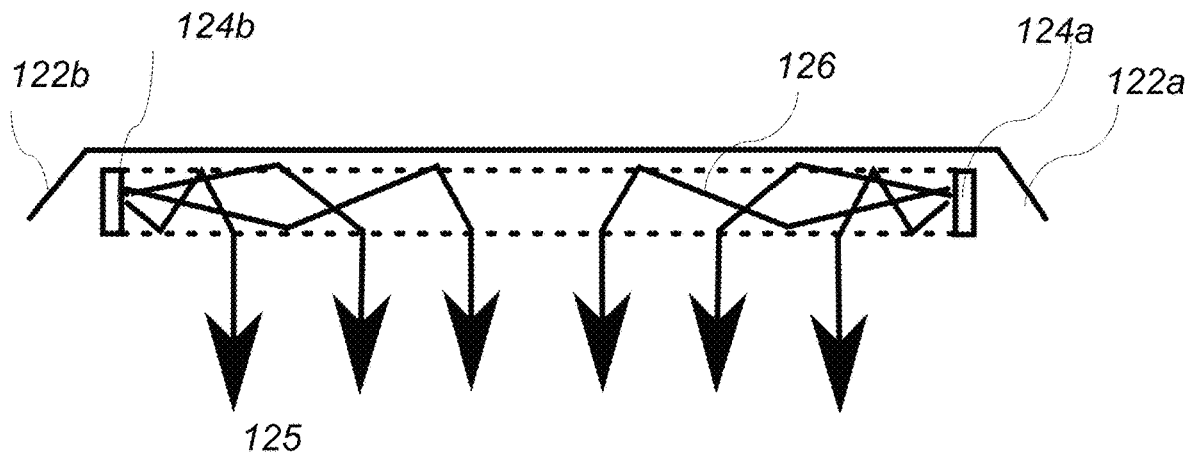
FIG. 2B is a cross-sectional view of the LED panel light of FIG. 2 along the A-A' plane.
Figure 3:
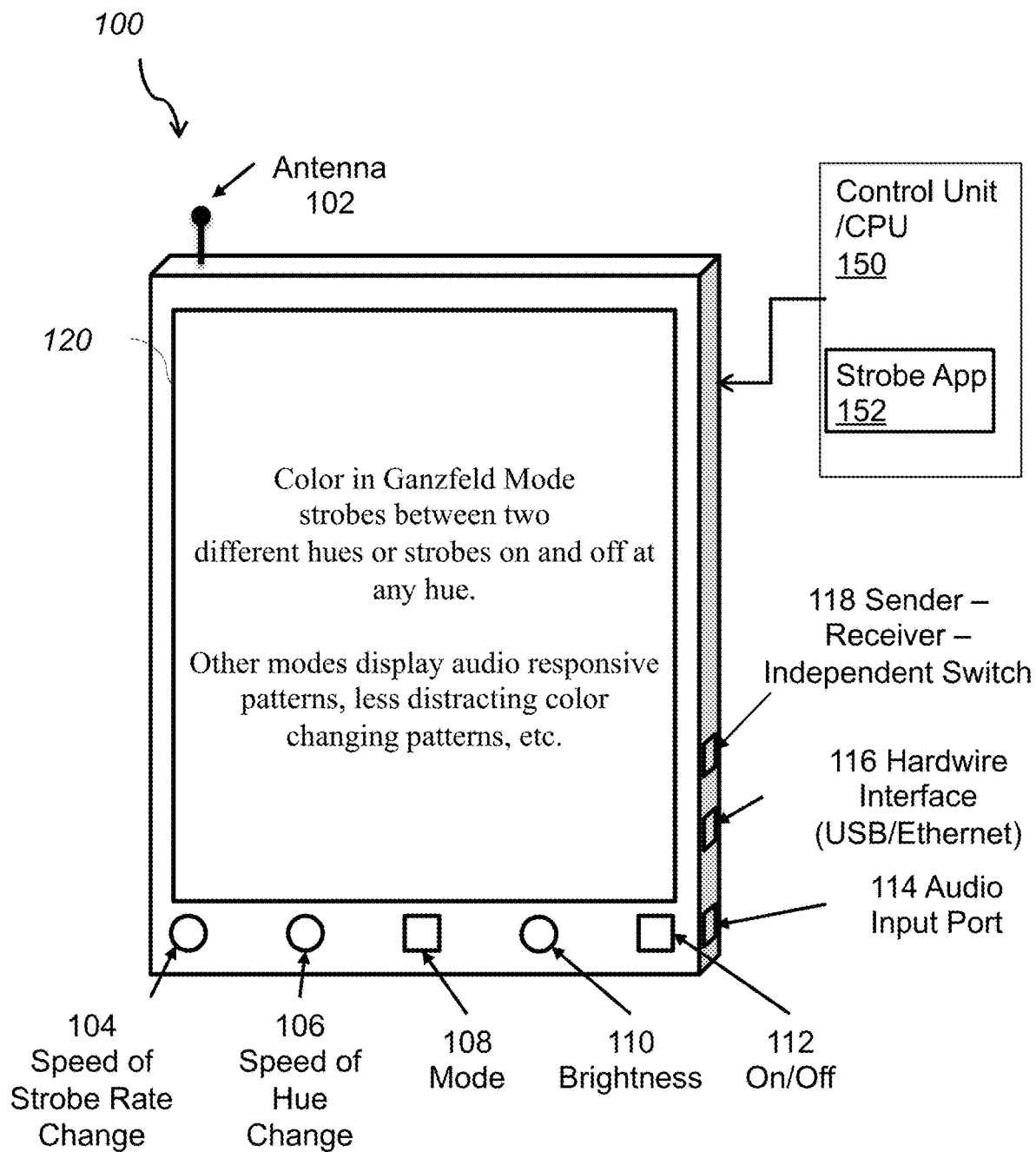
FIG. 3 is a system for generating the Ganzfeld effect according to this invention.

Referring to FIG. 3, a system 100 for generating a Ganzfeld effect includes a strobing flat LED panel light 120 and a control/CPU unit 150. The flat LED panel light 120 is an edge lit flat LED panel light. The edge lit flat LED panel light has LED strips 124b, 124a on the left and right edges 122b and 122a, respectively, a diffuser 126, and light is emitted from the panel along direction 125, as shown in FIG. 2A and FIG. 2B. The flat LED panel light may be a red-green-blue (RGB) or red-green-blue-white (RGBW) or other combinations of two or more colors. In one example the flat LED panel light is less than 12 inches thick and includes a diffuser layer 126 that makes the color uniform across the panel. The LED panel 120 also includes an antenna 102, a control for the speed of strobe rate change 104, a control for the speed of hue change 106, a control for the strobing or visualization mode 108, a control for the brightness of the panel 110, an On/Off switch 112, an audio input port 114, a hardware interface 116 (USB, Ethernet, among others), and a sender/receiver/independent switch 118. The emitted lighted 125 is a color changing strobe light that has a strobing rate in the range of 10 Hz to 60 Hz. This strobing rate triggers the Ganzfeld effect and is capable of generating vivid geometric patterns depending upon the strobing mode. The Ganzfeld effect is tiggered when a user standing in front of the strobing LED panel, provided the strobing LED panel light covers at least 5% of the user's field of view. There are several modes of strobing including strobing a single color/hue (e.g., red) on/off, or strobing between different colors/hues (red-green) with or without an off period between alternating hues. The strobe rate may vary smoothly over time and the LED panel may vary the color/hue smoothly over time. Control unit 150 includes a strobe application 152 that provides an automatic algorithm to shift the colors so that the image has varying apparent color ("purple to yellow" or "green to red" for example). Strobe application 152 also provides an automatic algorithm that varies the strobe rate in order to generate the Ganzfeld effect so that a person can see smoothly varying geometric patterns and colors. If the strobe rate remains static then the person sees a mostly non-dynamic (i.e., constant) pattern. The system may further include more than one LED panels 120 and the panels 120 may be wirelessly synchronized via a low-latency protocol that allows many lights to strobe synchronously.

Figure 4A:
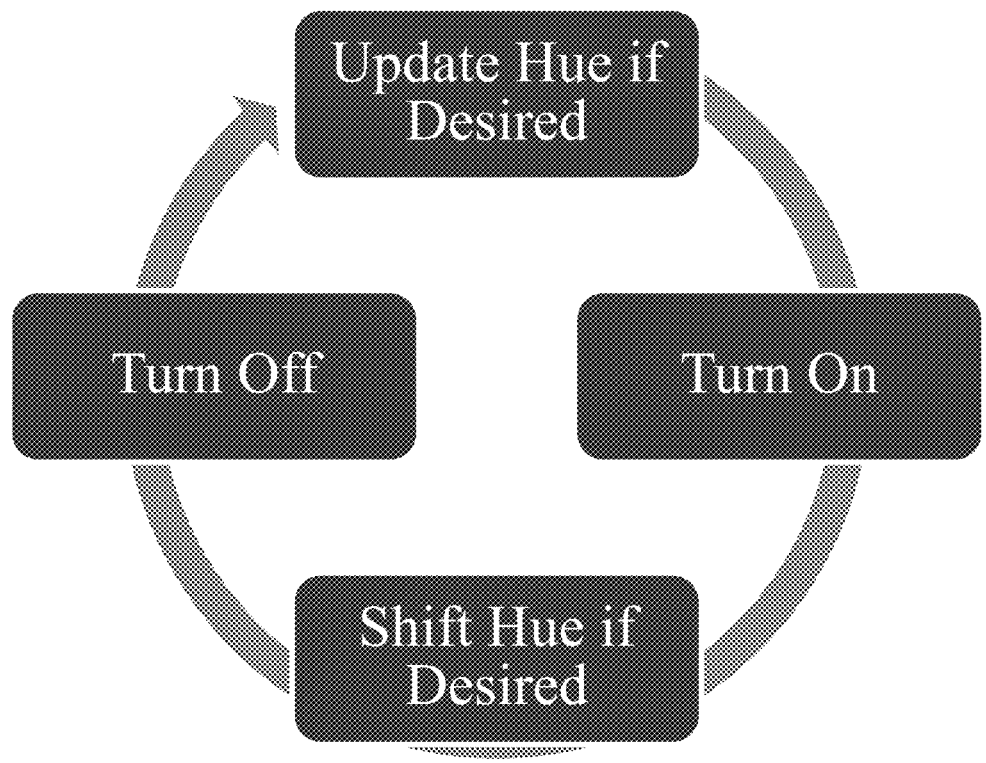
FIG. 4A depicts a first mode for generating the Ganzfeld effect using the system of FIG. 3, according to this invention.
Figure 4B:
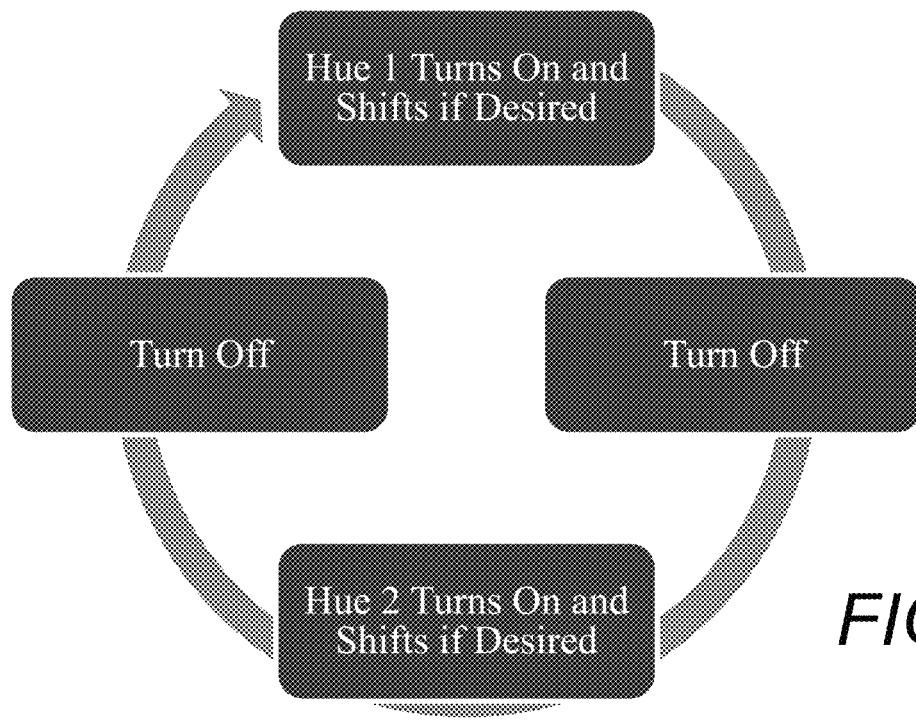
FIG. 4B depicts a second mode for generating the Ganzfeld effect using the system of FIG. 3, according to this invention.
Figure 4C:
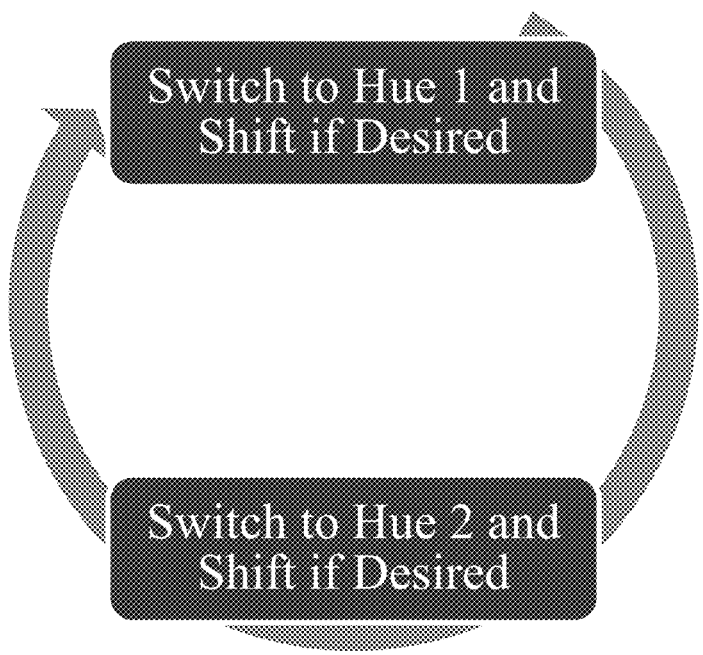
FIG. 4C depicts a third mode for generating the Ganzfeld effect using the system of FIG. 3, according to this invention.

Referring to FIG. 4A-FIG. 4C, a strobe light operating in the 10 Hz to 60 Hz frequency range is capable of triggering the visual cortex of the user to produce geometric patterns (Ganzfeld effect). The Ganzfeld effect works regardless of whether the light is strobing on and off at a single color/hue (Mode 1, FIG. 4A) or between different colors/hues. The two or more hues may alternate with an off period in between, as shown in Mode 2 FIG. 4B. Alternatively, the two or more hues may alternate with no off period in between, as shown in Mode 3 FIG. 4C.

Figure 5:
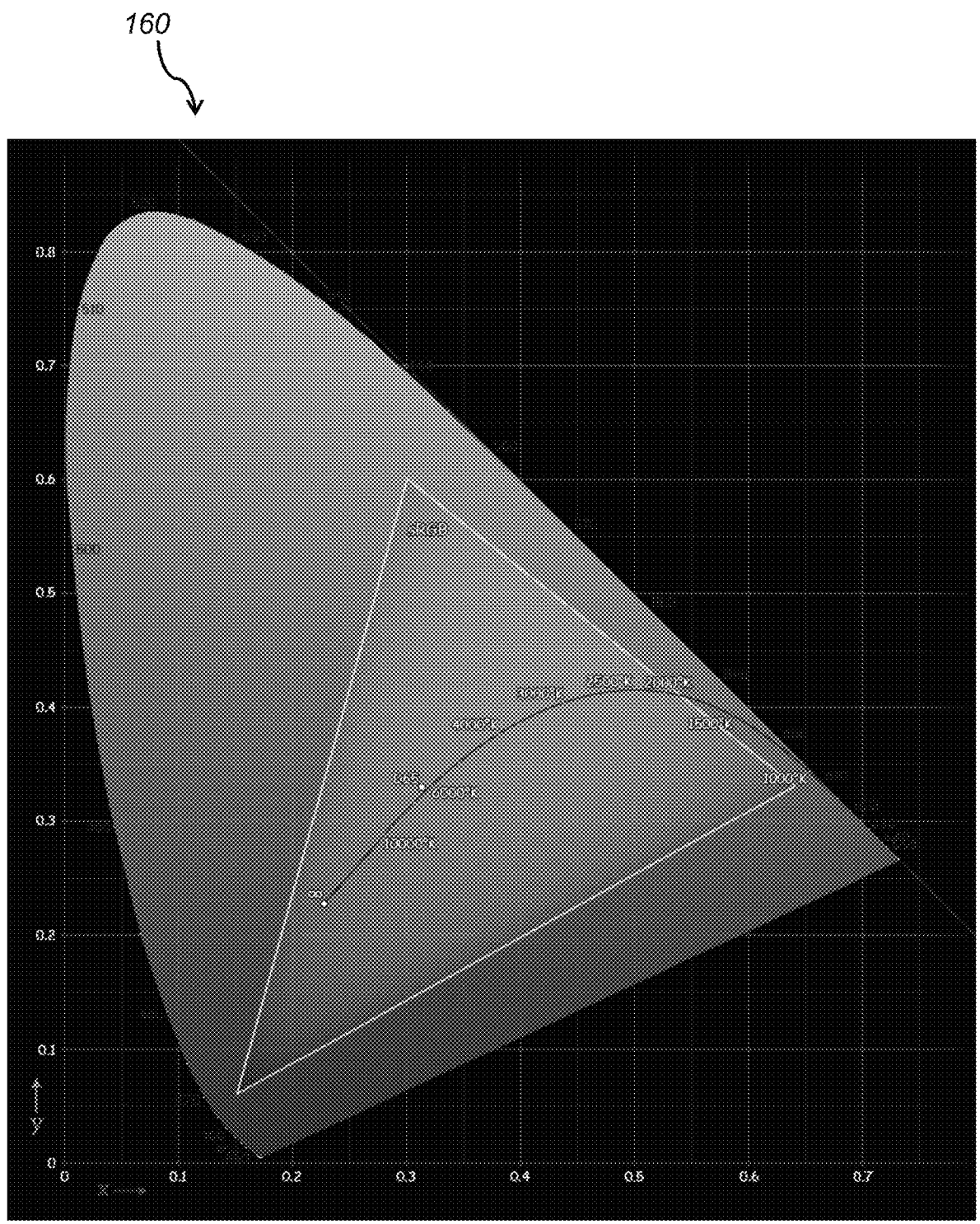
FIG. 5 depicts an xy-chromaticity diagram showing the gamut of the standard Red, Green and Blue (sRGB) color space and location of the primary colors.
Figure 6:
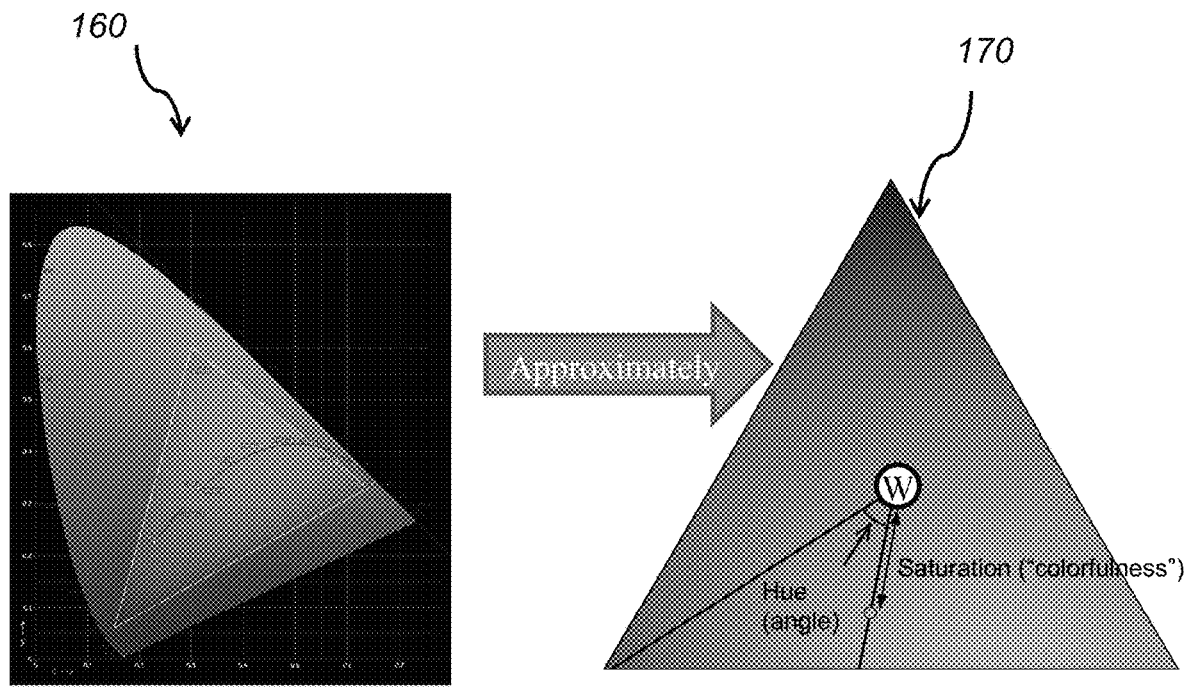
FIG. 6 depicts the transformation of the sRGB diagram of FIG. 5 to a simple triangle.

Referring to FIG. 5, in the International Commission on Illumination (CIE) standard red-green-blue (sRGB) Gamut of chromaticities 160, various whites are shown which may be used as white reference for hue. The triangle 170 demonstrates the gamut available to an example RGB LED system, shown in FIG. 6. Hue and saturation are one way to define the color. It is mathematically equivalent to any other method of defining a location in the color gamut. Hue represents the angle from the white point to the desired color, shown in FIG. 6, relative to a fixed color (typically red). Saturation represents how far from the white point the color is, also shown in FIG. 6. Frequently this color gamut is converted to a simple triangle 170 for mathematical simplicity with each LED color approximated as a pure red, green, or blue, shown in FIG. 6. However, a more complete calculation can readily be done using established mathematics if more accuracy is desired. In one implementation of this invention an algorithm was developed using the CIE LCH color-space, which included full compatibility with arbitrary numbers of LED CIE LCH emitter locations or white LEDs. For example, this accounts for the difference between "LED red" and "true red" and ensures that two colors a given hue apart will appear to be about as different regardless of what color they are (perceptually uniformly varying hue).

Figure 7:
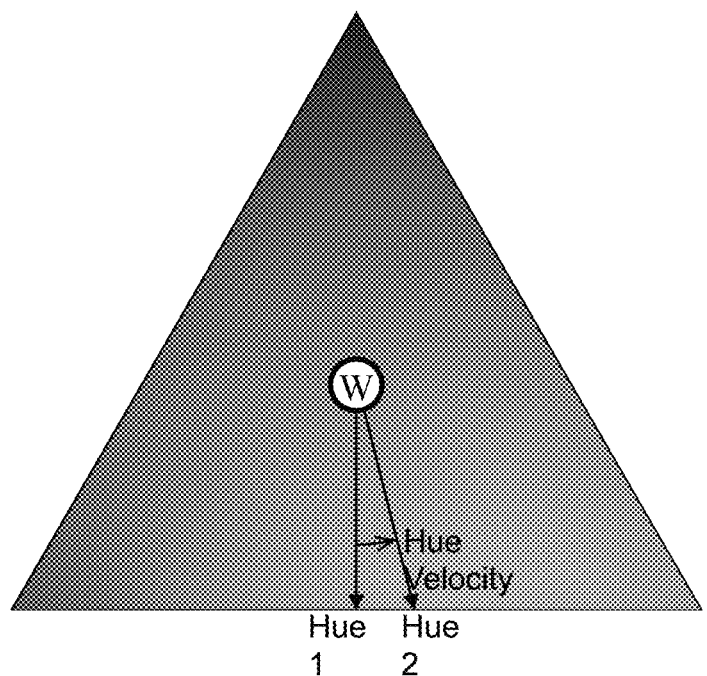
FIG. 7 depicts a first mode of the Ganzfeld implementation of hue shifting using hue velocity in the triangle diagram of FIG. 5.

Referring to FIG. 7, in the hue shifting mode using hue velocity (huevelocity), in each iterative step, the amount of hue change is based on the time (T) taken multiplied by the hue velocity (huevelocity). The hue velocity is varied by adding a randomly generated value scaled according to the "hue change rate" control (C). Maximum and minimum hue velocities are used to keep hue velocity in a reasonable range (scaled according to the "hue change rate" control). If the system is in a mode without strobing, a typical behavior is a slowly but smoothly varying hue. Hue velocity has "momentum" to avoid unpredictable hue changes ("jerks"). Typical operation uses 100% saturation for most intense colors.

Example 1

$$huevelocity_{i+1} = huevelocity_i * (1-C) + random * C$$

$$hue_{i+1} = hue_i + T * huevelocity_{i+1}$$

In this example, an exponential roll-off filter is shown as a way to low pass filter the hue velocity to provide "momentum" and keep it from varying too rapidly. Velocity is typically multiplied by a time to keep the hue shift consistent. In one example, the "hue change rate" (C) is in the range of zero to one and the random number is of the order of magnitude of the huevelocity.

In one example, Mode 1 of the Ganzfeld implementation is simulated as follows:

Example 2 updateLEDhue(hue+T*velocity change)
setLEDbrightness(1)
wait
setLEDbrightness(0)
wait
repeat Concept: Update the hue value, turn the light on, wait a calculated time, turn the light off, wait a calculated time, and repeat forever.

Figure 8:
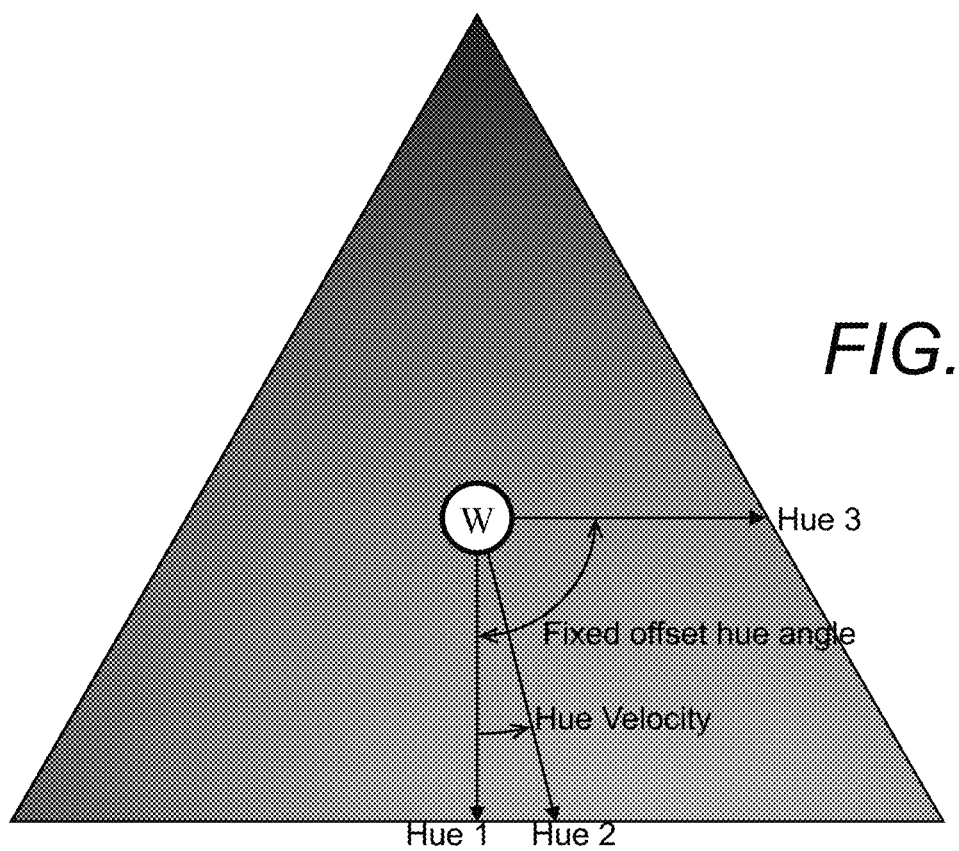
FIG. 8 depict a second mode of the Ganzfeld implementation of hue shifting using hue velocity in the triangle diagram of FIG. 5.

In one example, Mode 2 of the Ganzfeld implementation is simulated as follows:

Example 3 updateLEDhue(hue {+T*optional velocity change})
setLEDbrightness(1)
wait
setLEDbrightness(0)
wait
updateLEDhue(hue+offset {+T*optional velocity change})
setLEDbrightness(1)
wait
setLEDbrightness(0)
wait
repeat Concept: Update the hue value, turn on, turn off, and then shift by a fixed offset which is typically 90 to 270 degrees (assuming 360 degrees equals 0 degrees in hue), turn on, turn off, and then shift back to the first hue, optionally updating based on the hue velocity at each hue. In FIG. 8, these are labeled Hue 1 and Hue 3. The fixed angle remains constant, so if Hue 1 or Hue 3 is shifted, the other is shifted to match.

At each step, the hue may be updated based on the velocity. It happens at least once per cycle above. If more than two hues are used, they are alternated between in a pattern, with or without hue shifting at each step but with at least one per complete pattern.

In one example, Mode 3 of the Ganzfeld implementation is simulated as follows:

Example 4 updateLEDhue(hue {+T*optional velocity change})
wait
updateLEDhue(hue+offset {+T*optional velocity change})
wait
repeat Concept: In this mode the brightness is not turned on and off to produce strobing. Instead, two or more hues are rapidly alternated between, producing a similar effect.

Update the hue value, and shift by a fixed offset which is typically 90 to 270 degrees (assuming 360 degrees equals 0 degrees in hue), then shift back to the first hue, optionally updating based on the hue velocity at each step. In FIG. 8, these are labeled Hue 1 and Hue 3. The fixed angle remains constant, so if Hue 1 or Hue 3 is shifted, the other is shifted to match.

At each step, the hue may be updated based on the velocity. It happens at least once per cycle above. If more than two hues are used, they are alternated between in a pattern, with or without hue shifting at each step but with at least one per complete pattern.

The Ganzfeld implementation based on the speed of strobe rate change includes the following. The strobe rate is varied automatically between about 10 Hz and about 60 Hz. Varying the strobe rate enhances the dynamic effect of the Ganzfeld effect as the patterns will change and different people see the effect more with different frequency and hue combinations. More limited ranges are sometimes used for various reasons including reducing epilepsy risk or fine tuning of the effect. The strobe rate is varied by using a strobe velocity similarly to the hue velocity, which represents what appears like a "momentum" to the direction the strobe rate changes. By using something like an exponential rolloff filter, the strobe rate shifts slowly and smoothly with maximum and minimum strobe rate velocities respected.

Example 5

$$strobefrequencyvelocity_{i+1} = strobefrequencyvelocity_i * (1-C) + random*C$$

$$strobefrequency_{i+1} = strobefrequency_i + T*strobefrequencyvelocity_{i+1}$$

where the random number is of the same range as the strobefrequency and C controls how fast the velocity changes, with C being in the range of 0 to 1. In each iteration, the strobe frequency is updated using the velocity, typically multiplied by the time change to keep the strobe frequency change smoothly varying. An enhancement is to create a "bounce" where if the strobe frequency hits either limit it instantaneously reverses the strobe frequency velocity to keep the display dynamic rather than stuck at one limit or the other.

Wireless synchronization of more than one strobe panels is implemented as follows. This method enables the use of more than one strobe panel without physical connection between the two. The antenna is primarily used to synchronize strobing between multiple panels. The protocol in use is preferably point to multipoint with a single device controlling the strobe frequency of all panels, and is preferentially a low latency (<2 ms) networking protocol. Examples include FSK, BFSK, PSK, ASK, and other RF communication methods. In the simple example of Ganzfeld Method 1, at a 60 Hz strobe frequency a variation of 8 milliseconds puts the two panels out of phase such that one is off while the other is on. Two microcontroller clocks, even in the case of extreme accuracy and stability, will only have about 10 ppm stability and 10 ppm accuracy. In practice they are much worse than this. If two clocks differ by just 10 ppm, it only takes 13.3 minutes for two panels to be perfectly out of phase, necessitating a low latency method for resynchronizing clocks.

This can most easily be achieved by relying on a seeded pseudonumber generator to keep panels running deterministic code while sending out clock pulses over RF from one light to all other lights or from a central device to all lights which increments the onboard state. For example, when the controlling device determines it is time to be off, it emits an RF clock which all panels know means to turn off due to the mode configuration. When it is time to turn back on it emits an RF signal. At each of these steps, all panels perform an identical change to hue and strobe frequency due to the deterministic nature of a pseudorandom number generator without requiring any data transmission other than that there was a clock pulse. The mode must be known by all devices, and is preferentially transmitted wirelessly from the controlling device to ensure all panels are in the same state.

Upon switching between independent mode and sender/receiver mode using either a physical switch or automatically, the devices restart their random number generators using the same seed followed by responding to clock signals that cause each panel to update their state depending on the mode configured.

The system may also include an audio responsive mode, which is implemented as follows. The panel may include an audio input jack or microphone. If a microphone is used, it is best to use a low-pass filter such as the exponential rolloff filter to reduce the noise. This mode calls for the hue to shift either at a constant rate or a rate controlled by a hue velocity as described above. Beats are detected if the amplitude of the music increases faster (change in volume divided by change in time) than a set threshold. The amplitude must be calculated based on the RMS (root-mean square) or a similar measure as it is an AC signal. An exponential rolloff filter with a very long time constant can be easily used to estimate the DC offset of the audio signal and convert the reading to an estimate of the volume. The absolute value of the measured audio signal from this DC offset may also be used as a good measure of the volume with minimal processing power required. The beat detection threshold is slowly increased or decreased over time to reach a target number of beats per period of time (for example, minutes or seconds). This allows for the algorithm to readily work with fast, slow, loud, or quiet music as the detection threshold is automatically changed. In this mode, one control knob could be used to vary the target beats per minute while the second control knob varies the hue velocity. When a beat is detected, the panel brightness is increased and decreased. Typically, the brightness will go on quickly to produce the best visual effect with a slower decay, for instance turning on in <10 ms and off in >100 ms is appealing. Typically, the maximum brightness will be related to the volume of the beat relative to the typical volume of the music at the time. An exponential rolloff filter can be used to easily allow the music "typical volume" to be expanded immediately if a loud sound is heard and then slowly return to some default range over a period of time. As such, if the music is quiet and a loud beat is suddenly detected, the light will turn on to full brightness and subsequent not quite as loud beats will go up to a medium brightness. If the music is loud and a relatively quiet beat is detected, the light will turn on to a low brightness. By automatically varying the "typical volume" as audio signals are analyzed the system responds well when switching music genres, effectively implementing dynamic range compression (compression). Beats may overlap, in which case a newly detected beat will take priority over the original beat. This is readily accomplished by ramping up the brightness from whatever the current brightness is rather than expecting a brightness ramp to start from zero. When a beat is detected, the hue may additionally be varied in a pattern, such as by increasing the hue while the brightness goes up and then decreasing the hue while the brightness goes down to produce a "hue skipping" effect. In an alternative implementation, the brightness of the panel remains relatively constant and the hue is instead shifted when a beat is detected, for instance by skipping rapidly forward by 10 degrees (out of 360 degrees in a color wheel) on top of the base hue each time a beat is detected, optionally returning to the starting hue. This may be performed while the overall base hue is shifted according to the hue velocity whether shifting as in Example 1, or by varying the base hue at a constant rate. Alternatively, the volume of the music or beats per minute threshold (as a proxy for how many beats there could be if the threshold were lower) can be used to vary the hue velocity.

Referring to FIG. 3, the mode button 108 allows the user to change between different effects. For example:
  Ganzfeld Modes 1, 2, and 3.
  Varying hue and/or saturation without strobing.
  Varying brightness along with either hue or saturation to pulse different colors.
  Relying on audio input to provide audio signal for panel to respond to using algorithm on previous page.

In alternative modes, hue velocity 106 and strobe frequency velocity 104 knobs may be repurposed. For instance:
  The hue velocity knob 106 could control the speed of a color wheel while the strobe frequency velocity knob 104 could control the saturation.
  The hue velocity knob 106 could control how fast the hue changes in audio responsive mode while the strobe frequency velocity knob 104 could control the target beats per minute.

The brightness knob 110 changes the brightness of the LED panel. The On/Off switch 112 turns the LED panel display on and off, regardless of whether it fully powers off the actual device. The hardware interface 116 can be, for instance, USB from a computer used to modify the onboard code or control the panel remotely. The hardware interface may also be something like an ethernet port to allow the panel to be plugged into the internet. Each port or control or antenna may be entirely missing or hidden with no meaningful change in the concept. It is entirely feasible to remove all control buttons and still achieve the desired effect with a fully automatic or wireless program.

In one example, the LED panel strobe light is about two feet square and under twelve inches deep depending on the frame. The panel may be larger or smaller, to a limit based on the allowable brightness variation across the panel surface. In this example, the LED panel uses small LEDs around the edge of the frame shining into a thin piece of transparent material (acrylic) and a diffuser 126 piece of plastic placed over the transparent material with some padding. In one example, the transparent material has "scattering sites" at roughly 1 cm spacing to provide uniform brightness across the panel. In one example, the LED panel relies on one wire providing 24V, and uses a custom circuit board designed to connect each of the three return wires (red, green, blue) to ground such that current can flow through that chain of LEDs. In one example, individual RGB color brightnesses are controlled with pulse width modulation (PWM) by a microcontroller interfacing with the various knobs, antennas, and ports on the LED panel.

Other embodiments include one or more of the following. Other LED driving methods are used, such as three 24V wires and a single ground, two wires per color for cathode and anode, other voltages (12V or 48V for example), or current based control. The LED panel may be extended to RGBW or other LED color combinations. It is preferable to have at least three LED colors so that it is possible to vary the hue rather than mostly the saturation between the two available hues (or alternating between them). Similarly, a single color would also work as a strobe light.

Several embodiments of the present invention have been described. Nevertheless, it will be understood that various modifications may be made without departing from the spirit and scope of the invention. Accordingly, other embodiments are within the scope of the following claims.

What is claimed is:

1. A system for generating a Ganzfeld effect comprising:
a flat light emitting diode (LED) panel emitting a strobing light;
a controller comprising a control for a speed of a strobe rate change, and a control for a speed of a color change of the emitted strobing light;
wherein the controller controls the speed of the strobe rate change and/or the speed of the color change of the emitted strobing light so that the emitted strobing light is configured to generate geometric patterns in a visual cortex of a user standing in front of the flat LED panel, when the flat LED panel covers at least 5% of the user's field of view.

2. The system of claim 1, wherein the flat LED panel is an edge-lit flat LED panel that receives light from an edge along a plane of the flat LED panel and emits light out of the plane of the flat LED panel.

3. The system of claim 1, wherein the strobe rate varies in the range of 10 Hz to 60 Hz.

4. The system of claim 1, wherein the flat LED panel comprises a red-green-blue (RGB) panel, or a red-green-blue-white (RGBW) panel or other combinations of two or more color panels.

5. The system of claim 1, wherein the strobing light is generated by switching on/off a single color light.

6. The system of claim 1, wherein the strobing light is generated by switching between different colors with an off period between alternating colors or without an off period between alternating colors.

7. The system of claim 1, wherein the strobe rate varies over time.

8. The system of claim 1, further comprising a strobe application that provides computer implemented instruction for shifting the colors and hues of the strobing light and for varying the strobe rate in order to generate the geometric patterns in the visual cortex of the user.

9. The system of claim 1, further comprising additional LED panels and wherein all LED panels are wirelessly synchronized via a low-latency protocol that allows the LED panels to strobe synchronously.

10. The system of claim 1, further comprising an antenna, an audio input port, an on/off switch, a sender, a receiver, hardware interfaces, and controls for strobing or visualization mode, and brightness of the LED panel.

11. The system of claim 1, further comprising an audio signal input and an audio analysis application and wherein the audio analysis application detects beats in the audio signal and varies a beat detection threshold to target a specified number of beats per second and wherein the detected beats are used to time-modulate color, hue, saturation, brightness or the strobe rate of the emitted strobing light.

12. A method for generating a Ganzfeld effect comprising:
providing a flat light emitting diode (LED) panel and emitting a strobing light via the LED panel;
providing a controller comprising a control for a speed of a strobe rate change, and a control for a speed of a color change of the emitted strobing light; and
controlling the speed of the strobe rate change and/or the speed of the color change of the emitted strobing light so that the emitted strobing light generates geometric patterns in a visual cortex of a user standing in front of the flat LED panel, when the flat LED panel covers at least 5% of the user's field of view.

13. The method of claim 12, wherein the flat LED panel is an edge-lit flat LED panel that receives light from an edge along a plane of the flat LED panel and emits light out of the plane of the flat LED panel.

14. The method of claim 12, wherein the strobe rate varies in the range of 10 Hz to 60 Hz.

15. The method of claim 12, wherein the flat LED panel comprises a red-green-blue (RGB) panel, or a red-green-blue-white (RGBW) panel or other combinations of two or more color panels.

16. The method of claim 12, wherein the strobing light is generated by switching on/off a single color light.

17. The method of claim 12, wherein the strobing light is generated by switching between different colors with an off period between alternating colors or without an off period between alternating colors.

18. The method of claim 12, wherein the strobe rate varies over time.

19. The method of claim 12, further comprising providing a strobe application that provides computer implemented instruction for shifting the colors and hues of the strobing light and for varying the strobe rate in order to generate the geometric patterns in the visual cortex of the user.

20. The method of claim 12, further comprising providing additional LED panels and wirelessly synchronizing all LED panels via a low-latency protocol that allows the LED panels to strobe synchronously.

21. The method of claim 12, further comprising providing an antenna, an audio input port, an on/off switch, a sender, a receiver, hardware interfaces, and controls for strobing or visualization mode, and brightness of the LED panel.

22. The method of claim 12, further comprising providing an audio signal input and an audio analysis application and wherein the audio analysis application detects beats in the audio signal input and varies a beat detection threshold to target a specified number of beats per second and wherein the detected beats are used to time-modulate color, hue, saturation, brightness or the strobe rate of the LED panel light.

* * * * *